United States Patent [19]

Baker et al.

[11] Patent Number: 5,399,558

[45] Date of Patent: Mar. 21, 1995

[54] ISOFLAVONOID ANTIBACTERIAL COMPOUNDS, COMPOSITIONS AND USE

[75] Inventors: William R. Baker, Bellevue, Wash.; Lester A. Mitscher, Lawrence, Kans.

[73] Assignee: PathoGenesis Corporation, Seattle, Wash.

[21] Appl. No.: 157,619

[22] Filed: Nov. 24, 1993

[51] Int. Cl.6 .................. A61K 31/35; A61K 31/535; C07D 493/04

[52] U.S. Cl. ................................ 514/232.5; 514/253; 514/468; 544/79; 544/357; 546/256; 546/270; 549/214; 549/383

[58] Field of Search .......................... 544/79; 549/383; 514/468

[56] References Cited

FOREIGN PATENT DOCUMENTS 227640 9/1988 Japan .

OTHER PUBLICATIONS

Mitscher, L. et al., "A Modern Look At Folkloric Use Of Anti-Infective Agents," *J. Natural Products* 50(6):1025-1040 (1987).
Mitscher, L. et al., "Antimicrobial Pterocarpans of Nigerian *Erythrina Mildbraedii*," *Phytochemistry* 27(11):3449-3452 (1988).
Mitscher, L. et al., "Erycristin, A New Antimicrobial Petrocarpan From *Erythrina Crista-Galli*," *Phytochemistry* 27(2):381-385 (1988).
O'Neill, M. J. et al., "Inducible Isoflavonoids From The Lima Bean, *Phaseolus Lunatus*," *Phytochemistry* 25(6):1315-1322 (1986).
Kamat, V. S. et al., "Antimicrobial Agents From An East African Medicinal Plant *Erythrina Abyssinica*," *Heterocycles* 15(2)1163-1170 (1981).
Iinuma, M. et al., "Phenolic Constituents in *Erythrina x bidwilli* and Their Activity against Oral Microbial Organisms," *Chem. Pharm. Bull.* 40(10):2749-2752 (1992).
Telikepalli, H. et al., "Isoflavonoids And A Cinnamyl Phenol From Root Extracts Of *Erythrina Variegata*," *Phytochemistry* 29(6):2005-2007(1990).
Engler, T. A. et al., "Stereoselective Syntheses of Three Different Classes of Neolignans From the Same Starting Materials," *Tetrahedron Letters* 34(9):1429-1432 (1993).
Engler, T. A. et al., "Synthetic Pterocarpans with Anti-HIV Activity," *Bioorganic & Medicinal Chemistry Letters* 3(6):1229-132 (1993).
Coelho, A. L. et al., "A Convenient Synthesis of (±)-4-Prenylpterocarpin," *Synthesis* 914-916 (1992).
Engler, T. A. et al., "Asymmetric Induction in Reactions of Styrenes With 1,4-Benzoquinones Utilizing Chiral Ti(IV) Complexes," *J. Am. Chem. Soc.* 113(13):5068-5070 (1991).
Narkhede, D. D. et al., "Total Synthesis of (±)-Leiocarpin and(±)-Isohemileiocarpin," *Tetrahedron* 46(6):2031-2034 (1990).
Engler, T. A. et al., "Formal 2+2 and 3+2 Cycloaddition Reactions of 2H-Chromenes with 2-Alkoxy-1,4-benzoquinones: Regioselective Synthesis of Substituted Pterocarpans," *J. Org. Chem.* 55(4):1248-1254 (1990).
Engler, T. A. et al., "A New Regioselective Synthesis of Pterocarpans," *J. Chem. Soc., Chem. Commun.* 454-455 (1989).
Breytenbach, J. C. and Rall, G. J. H., "Structure and Synthesis of Isoflavonoid Analogues from *Neorautanenia amboensis* Schinz," *J. Chem. Soc., Perkin I* 1804-1809 (1980).
Horino, H. and Inoue, N., "A New Route to Chromanocoumarans. Synthesis of (±)-Pterocarpin," *J. Chem. Soc., Chem. Commun.* 500-501 (1976).
Taniguchi, M. and Kubo, I., "Ethnobotanical Drug Discovery Based on Medicine Men's Trials in the African Savanna: Screening of East African Plants for Antimicrobial ActivityII," *J. Nat. Prod.* 56(9):1539-1546 (1993).

*Primary Examiner*—Robert W. Ramsuer
*Attorney, Agent, or Firm*—Christensen, O'Connor, Johnson & Kindness

[57] ABSTRACT

Methods, compounds and compositions are provided for inhibiting the growth of mycobacteria and gram-positive organisms in vitro and of treatment of mycobacterial and gram-positive infections in vivo using compounds of the formula (I) or (II):

(Abstract continued on next page.)

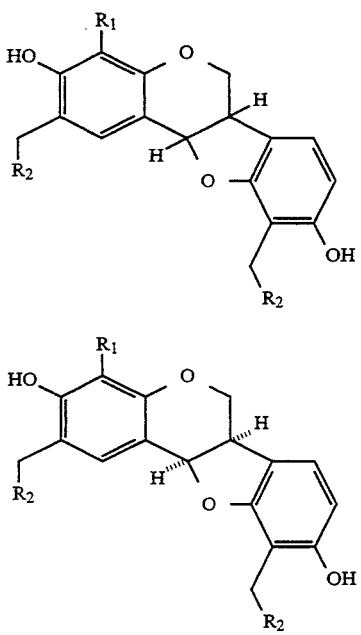

wherein $R_1$ is hydrogen, halogen, amino or loweralkyl; and $R_2$ is selected from the group consisting of —$CONR_4R_5$, —$(CH_2)_n$—$NR_4R_5$, —NHCO—$NR_4R_5$ and —$NHCO_2R_4$, wherein $R_4$ and $R_5$ are selected from hydrogen, loweralkyl, alkoxy, cycloalkyl, cycloalkylalkyl, aryl, arylalkyl, arylalkylaryl, arylaryl, aryoxy, aryloxyaryl, aryloxyarylalkyl, arylalkoxy, arylalkoxyaryl, arylalkoxyarylalkyl, arylalkoxyaryl, alkenyl, alkynyl and heterocycle, or $R_4$ and $R_5$ are connected to form a ring and produce cycloalkyl or heterocycle; and n is 0, 1, 2, or 3; or a pharmaceutically acceptable salt thereof processes for the preparation of the compounds of the invention in addition to intermediates useful in these processes, a pharmaceutical composition, and a method of treating disorders resulting from mycobacterial or MRSA infections. The methods, compounds and compositions are particularly useful for inhibiting the growth of *Mycobacterium tuberculosis*, and may be used alone, or in combination with other anti-*Mycobacterium tuberculosis* agents, such as isoniazid, rifampin, pyrazinamide, rifabutin, streptomycin and ciprofloxacin, to provide new agents for the treatment of tuberculosis, including multidrug-resistant tuberculosis (MDRTB).

19 Claims, 1 Drawing Sheet

ISOFLAVONOID ANTIBACTERIAL COMPOUNDS, COMPOSITIONS AND USE

FIELD OF THE INVENTION

The present invention relates to new isoflavonoid compounds which are useful in killing mycobacteria and gram-positive organisms, to antibacterial compositions containing the compounds and to the use of the compounds and compositions, alone or in combination with other antimicrobial agents, in the treatment of pathogenic mycobacterial and gram-positive bacterial infections.

BACKGROUND OF THE INVENTION

*Mycobacterium tuberculosis* infections are on the rise. In the United States, it is estimated that over 28,000 new cases of tuberculosis were recorded over the last seven years. TB is highly contagious and it possesses a profound threat to public health. The increase of HIV infection has further complicated the spread of the disease since tuberculosis is the predominate mycobacterial infection in HIV-infected individuals. In addition, the resistance of *M. tuberculosis* to first-line drugs is also growing. Prior to 1984, only about 10 percent of TB bacteria isolated from patients in the United States were resistant to even a single antibacterial drug. In 1984, 52 percent of patients were infected with tubercle bacilli resistant to at least one drug, and 32 percent were resistant to one or more drugs. Ten percent of the recorded multidrug resistant (MDR) TB cases to date have occurred in previously healthy people whose mortality rate, 70 to 90 percent, has been nearly the same as that of immunosuppressed persons with MDRTB. *M. tuberculosis* is not the only mycobacterial infection on the increase. The rates of *M. avium* and *M. fortuitium-M. chelonae* infections in AIDS and non-AIDS patients are also increasing. Thus, new chemotherapeutic agents to treat mycobacterial infections especially the drug-resistant strains are needed and must be developed as soon as possible.

After a decline in rates of infection over several decades, a disturbing increase in the incidence of tuberculosis (TB) is occurring. Because TB is highly contagious it poses a profound threat to public health. TB bacteria are easily passed from person to person in airborne droplets formed when a person with active TB sneezes or coughs.

Even more alarming has been the rise of multidrug-resistant tuberculosis (MDRTB). Prior to 1984, about 10 percent of TB bacteria isolated from patients in the United States were resistant to even a single antibacterial drug. In 1984, 52 percent of patients were infected with *Mycobacterium tuberculosis* (also referred to as tubercle bacilli) resistant to at least one drug, and 32 percent were resistant to one or more drugs. Outbreaks of MDRTB have been reported in 13 states. Ten percent of the recorded MDRTB cases to date have occurred in previously healthy people whose mortality rate—70 to 90 percent—has been nearly the same as that of immunosuppressed persons with MDRTB (Snider and Roper, 1992).

The United States Centers for Disease Control (CDC) has released preliminary results of a joint study with the New York State Health Department showing that cases of drug-resistant TB have more than doubled since 1984. CDC data from the first quarter of 1991 show that many of these drug-resistant strains are resistant to both of the front-line TB drugs, rifampin and isoniazid. Outbreaks of MDRTB have occurred in hospitals in Miami and New York City, as well as in the New York State prison system. In one hospital in New York City, the median-interval between diagnosis of MDRTB and death was only four weeks. Additional clusters of MDRTB were reported to the CDC in 1990 and 1991 from Mississippi, Missouri, and Michigan.

There are five front-line drugs known to be highly effective against *Mycobacterium tuberculosis* and five second-line drugs that can be used when resistance to one or more of the front-line drugs is detected. Ironically, in the United States, until April 1992, there were shortages of antituberculosis drugs, some of which are crucially needed when resistance to the front-line drugs rifampin and isoniazid is present. These shortages had occurred because several pharmaceutical companies had ceased production of these drugs.

Because of its persistence in the body, the tubercle bacillus is a notoriously difficult pathogen to control. Although bacille Calmette-Guerin (BCG) vaccine protects against severe tuberculosis meningitis and disseminated TB in children, its efficacy against pulmonary TB in adults has varied widely in different parts of the world. Treatment of conventional TB is effective, but expensive, requiring daily treatment with multiple drugs for a minimum of six months. There is a universal tendency among TB patients to stop taking their drugs when the drugs begin to have their beneficial effect or to take the medications only intermittently. When this happens, relapses are frequent and very often are caused by drug-resistant tubercle bacilli that have survived the initial course of treatment. The emergence of drug-resistant *M. tuberculosis* is in many ways an index of individual compliance with antituberculosis chemotherapy and of the inability of the health care infrastructure to ensure adequate treatment. Many public health agencies that once could play key roles in this process have had their budgets cut drastically in recent years and hence are unable to perform this crucial service.

MDRTB is extraordinarily difficult to treat, and a majority of patients do not respond to therapy. Total treatment costs for an individual with MDRTB can be as much as ten times the cost of traditional treatment; the cost of the treatment drugs alone can be as much as 21 times as great.

The preferred treatment for classical TB consists of isoniazid, rifampin, and pyrazinamide. For patients whose tubercle bacilli are thought to be resistant to isoniazid, a fourth drug, ethambutol, is commonly added to the regimen until drug susceptibility results are known. Isolates of tubercle bacilli resistant to both isoniazid and rifampin, now representing about 20 percent in some cities, require specialized treatment with additional medications, which may include streptomycin and ciprofloxacin for almost two years.

The tubercle bacillus is a slow-growing organism. Three to six weeks are needed to grow the bacteria in the clinical laboratory, and an additional three to six weeks are needed to screen for antibiotic resistance. Such extended laboratory procedures can result in a delay in diagnosis, which means that patients with unrecognized drug-resistant TB may be treated ineffectively and remain infectious for a longer period. In HIV-positive individuals, MDRTB usually causes death within 4 to 16 weeks after being diagnosed, which is often before laboratory tests on drug susceptibility and resistance can be completed.

There is no evidence that mutation rates in *M. tuberculosis* organisms have increased or that increased virulence is to blame for the recent deadly outbreaks of TB. It is likely that drug-resistant forms of tuberculosis arose because of patient noncompliance with the 6- to 12-month regimen of antibiotics required to treat TB. Ineffective treatment regimens also play a role in the rising incidence of TB. To address noncompliance, some states with high TB rates are considering approaches to outreach, such as expanding directly observed therapy (DOT); others may reestablish inpatient facilities similar to the TB sanatoria of the first half of this century. Standard treatment regimens for TB have also been updated. Instead of taking two or three antibiotics, TB patients now take four. Still, as noted earlier, the current shortages of antituberculosis drugs in the United States have made even standard treatment difficult.

Erythrabyssin II is an pterocarpan-backbone isoflavonoid compound that occurs naturally in the root and stem bark of various species of Erythrina and has the following structure:

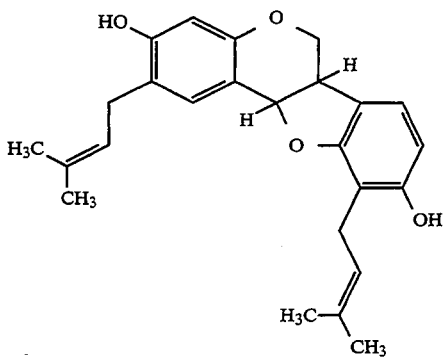

Erythrabyssin II has been reported by several investigators to exhibit weak antibacterial activity against *Staphylococcus aureus, Bacillus subtilis, Micrococcus lysodeikticus,* and nonpathogenic *Mycobacterium smegmatis.* See, for example, L. Mitscher et al. *J. Natural Products* 50:1025–1040, 1987, *Phytochemistry* 27:3449–52, 1988, and *Phytochemistry* 27:381–385, 1988; M. O'Neill et al. *Phytochemistry,* 25:13 15–22, 1986; K. Nakanishi et al. *Heterocycles,* 15:1163–70, 1981; and M. Iinuma, *Chem. Pharm. Bull.,* 40:2749–52, 1992.

There has been no suggestion in the art that various amine-based derivatives of erythrabyssin II would have antibacterial properties or be effective in the treatment of tuberculosis, including MDRTB.

SUMMARY OF THE INVENTION

It has now been surprisingly discovered that mycobacteria and gram-positive organisms can be controlled in vitro or in vivo by new erythrabyssin II isoflavonoid derivatives having the following structure (I):

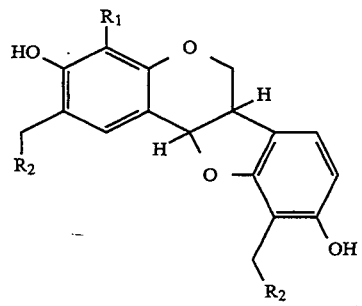

wherein $R_1$ is hydrogen, halogen, amino or loweralkyl; and $R_2$ is $-CONR_4R_5$, $-(CH_2)_n-N-R_4R_5$, or $-NH-CO-NR_4R_5$ wherein $R_4$ and $R_5$ are selected from hydrogen, loweralkyl, cycloalkyl, cycloalkylalkyl, aryl, arylalkyl, aryloxyaryl, aryloxyarylalkyl, arylalkoxyarylalkyl, arylalkoxyaryl, alkenyl, alkynyl and heterocycle, or $R_4$ and $R_5$ are connected to form a ring and produce cycloalkyl or heterocycle; and n is 0, 1, 2, or 3; or a pharmaceutically acceptable salt thereof. Accordingly, the present invention provides new compounds, new pharmaceutical compositions and new methods of inhibiting the growth of mycobacteria and gram-positive organisms in vitro and of treatment of mycobacterial and gram-positive organism infections in vivo using the new compounds and compositions.

In a presently preferred embodiment for the treatment of tuberculosis, the methods and compounds of the invention may be employed alone, or in combination with other anti-*Mycobacterium tuberculosis* agents, such as isoniazid, rifampin, pyrazinamide, rifabutin, streptomycin and ciprofloxacin, to provide new agents for the treatment of tuberculosis, including MDRTB.

BRIEF DESCRIPTION OF THE DRAWINGS

The foregoing will become more readily understood by reference to the following detailed description, taken in conjunction with the accompanying drawings, wherein.

DETAILED DESCRIPTION OF THE PREFERRED EMBODIMENT

Figure 1:
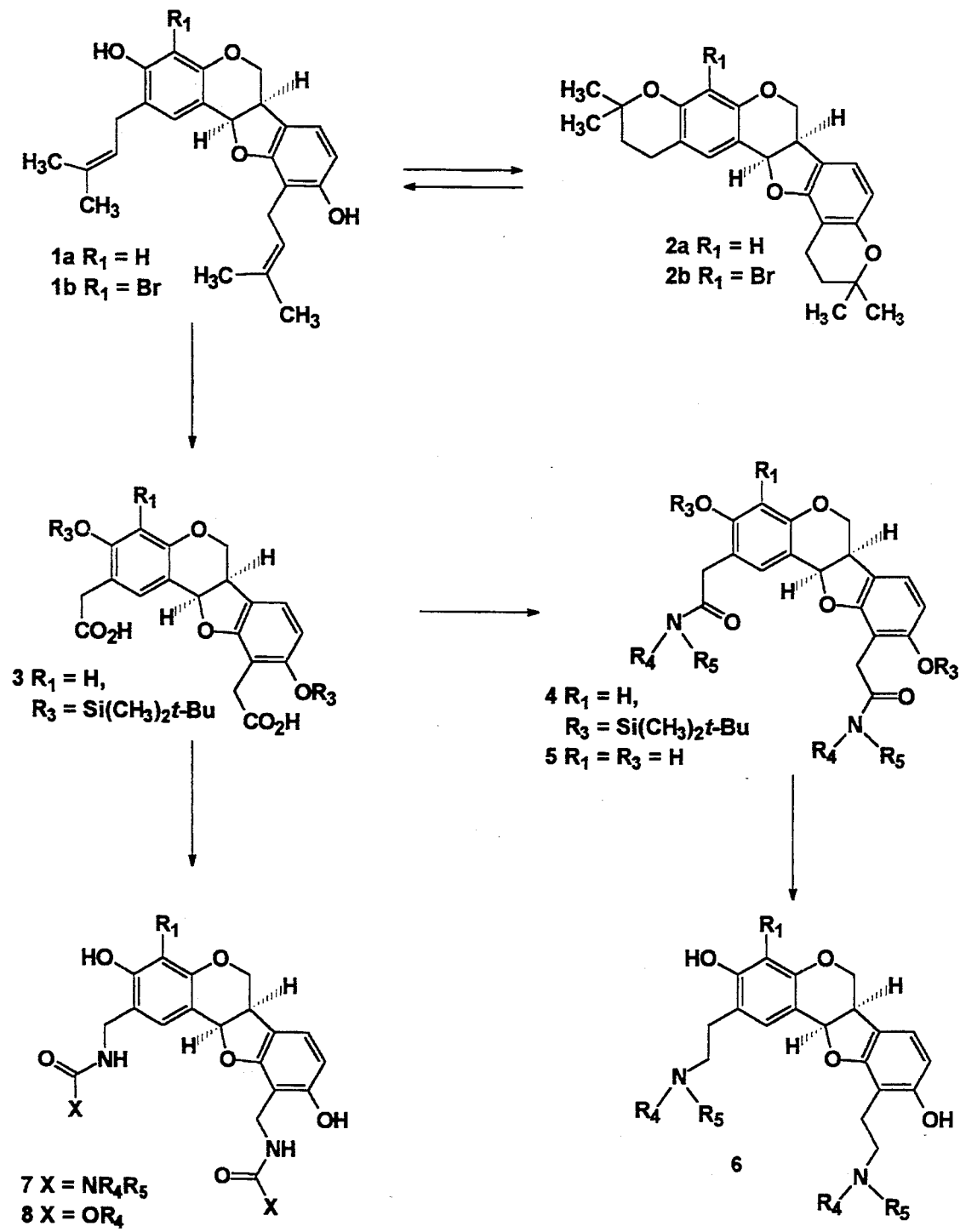
FIG. 1 is a schematic representation of alternative synthesis pathways of the compounds of the invention.

In accordance with the present invention there are provided compounds of formula (I):

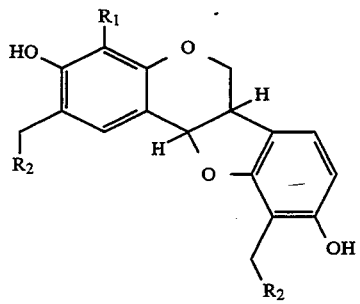

wherein $R_1$ is hydrogen, halogen, amino or loweralkyl and $R_2$ is $-CONR_4R_5$, $-(CH_2)_n-NR_4R_5$, $-NH-CO-NR_4R_5$ or $-NHCO_2R_4$, wherein $R_4$ and $R_5$ are selected from hydrogen, loweralkyl, alkoxy, cycloalkyl, cycloalkylalkyl, aryl, arylalkyl, arylalkylaryl, arylaryl, aryoxy, aryloxyaryl, aryloxyarylalkyl, arylalkoxy, arylalkoxyaryl, arylalkoxyarylalkyl, arylalkoxyaryl, alkenyl, alkynyl and heterocycle, or $R_4$ and $R_5$ are connected to form a ring and produce cycloalkyl or heterocycle; and n is 0, 1, 2, or 3; and the pharmaceutically acceptable salts thereof.

Presently preferred compounds of the invention are compounds of formula (II):

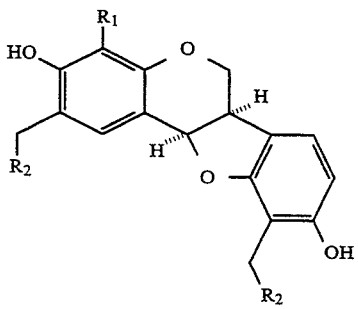

wherein $R_1$ and $R_2$ are as defined above; or a pharmaceutically acceptable salt thereof.

Presently particularly preferred compounds of the invention are compounds of formula (I) or (II) wherein $R_2$ is —CONR$_4$R$_5$ wherein $R_4$ and $R_5$ are selected from hydrogen, loweralkyl, cycloalkyl, cycloalkylalkyl, aryl, arylalkyl, aryloxyaryl, aryloxyarylalkyl, arylalkoxyarylalkyl, arylalkoxyaryl, alkenyl and alkynyl, or $R_4$ and $R_5$ are taken together to form cycloalkyl or heterocycle; and $R_1$ is hydrogen or halogen; more preferably $R_4$ and $R_5$ is selected from loweralkyl, aryloxyarylalkyl, alkenyl or alkynyl, or $R_4$ and $R_5$ are taken together to form cycloalkyl. Representative presently particularly preferred compounds of the invention are obtained when $R_4$ and $R_5$ are methyl or 3-methyl-2-butenyl, and $R_1$ is hydrogen.

In a further aspect of the present invention are disclosed pharmaceutical compositions are provided which comprise a compound of the present invention, either alone or together with one or more other antiinfective agents, in combination with a pharmaceutical acceptable carrier.

In accordance with another aspect of the present invention, methods are provided for control of mycobacteria and gram-positive organisms, either in vitro or in vivo. Thus, in one aspect the present invention provides a method of inhibiting the growth of mycobacterium or gram-positive organisms in vitro comprising contacting the Mycobacterium sp. with a growth inhibitory amount of a compound of the formula (I) or formula (II). In yet another aspect, the present invention provides methods of treating human or animal subjects suffering from a mycobacterial or gram-positive organism infection, e.g., tuberculosis, whether of sensitive-strain or multi-drug resistant strain (MDRTB) origin. Thus, the present invention provides a method of treating a human or animal subject in need of such treatment comprising administering to the subject a therapeutically effective amount of a compound of formula (I) or (II), above, either alone or in combination with other antiinfective agents.

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 Recommendations for Section E, Fundamental Stereochemistry, Pure Appl. Chem. 45:13–30, 1976. The terms a and b are employed for ring positions of cyclic compounds. The a-side of the reference plane is that side on which the preferred substituent lies at the lowered numbered position. Those substituents lying on the opposite side of the reference plane are assigned b descriptor. It should be noted that this usage differs from that for cyclic stereoparents, in which "a" means "below the plane" and denotes absolute configuration. The terms a and b configuration, as used herein, are as defined by the Chemical Abstracts Index Guide-Appendix IV (1987) paragraph 203.

The term "loweralkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to RO— wherein R is loweralkyl as defined above. Representative examples of lower alkoxy groups include methoxy, ethoxy, t-butoxy and the like.

The term "alkenyl" as used herein refers to a branched or straight chain comprising two to twenty carbon atoms which also comprises one or more carbon-carbon double bonds. Representative alkenyl groups include 2-propenyl (i.e., allyl), 3-methyl-2-butenyl, 3,7-dimethyl-2,6-octadienyl, 4,8-dimethyl-3,7-nonadienyl, 3.7.11-trimethyl-2,6,10-dodecatrienyl and the like.

The term "alkynyl" as used herein refers to a branched or straight chain comprising two to twenty carbon atoms which also comprises one or more carbon-carbon triple bonds. Representative alkynyl groups include ethynyl, 2-propynyl (propargyl), 1-propynyl and the like.

The term "aryl" as used herein refers to a phenyl or a $C_9$ or $C_{10}$ bicyclic carbocyclic ring system having one or more aromatic rings, including naphthyl, tetrahydronaphthyl, indanyl, indenyl and the like. Aryl groups can be unsubstituted or substituted with one, two or three substituents independently selected from loweralkyl, haloalkyl, alkoxy and halo.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylaryl" as used herein refers to an arylalkyl group as previously defined appended to an aryl group. Representative arylalkylaryl groups include 4-benzylphenyl, 3-benzylphenyl, 4-phenethylphenyl and the like.

The term "arylaryl" as used herein refers to an aryl group as previously defined which is appended to an aryl group. Representative arylaryl groups include biphenyl, 4-(1-naphthyl)phenyl, 4-(2-naphthyl)phenyl and the like.

The term "aryloxy" as used herein refers to $R_{20}$— wherein $R_{20}$ is an aryl group. Representative arylalkoxy group include benzyloxy, phenylethoxy and the like.

The term "arylalkoxy" as used herein refers to a lower alkoxy radical to which is appended an aryl group. Representative arylalkoxy group include benzyloxy, phenylethoxy and the like.

The term "aryloxyaryl" as used herein refers to an aryl radical to which is appended an aryloxy group. Representative aryloxyaryl groups include 4-phenoxyphenyl, 3-phenoxyphenyl, 4-phenoxy-1-naphthyl, 3-phenoxy-1-naphthyl and the like.

The term "aryloxyarylalkyl" as used herein refers to an arylalkyl radical to which is appended an aryloxy group. Representative aryloxyarylalkyl groups include 4-phenoxyphenylmethyl, 3-phenoxyphenylmethyl, 4-phenoxyphenylethyl, 3-phenoxyphenylethyl and the like.

The term "arylalkoxyaryl" as used herein refers to an aryl radical to which is appended an arylalkoxy group. Representative arylalkoxyaryl groups include 4-benzyloxyphenyl, 3-benzyloxyphenyl and the like.

The term "arylalkoxyarylalkyl" as used herein refers to an arylalkyl radical to which is appended an arylalkoxy group. Representative arylalkoxyarylalkyl groups include 4-benzyloxylbenzyl, 3-benzyloxybenzyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "halogen" or "halo" as used herein refers to iodo, bromo, chloro or fluoro.

The term "heterocycle" as used herein refers to an aromatic ring system composed of 5 or 6 atoms selected from the heteroatoms nitrogen, oxygen, and sulfur. The heterocycle maybe composed of one or more heteroatoms that are either directly connected such as pyrazole or connected through carbon such as pyrimidine. Heterocycles can be substituted or unsubstituted with one, two or three substituents independently selected from amino, alkylamino, halogen, alkylacylamino, loweralkyl. aryl, alkoxy.

The term "substituted heterocycle" or heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0–2 double bounds and the 6-membered ring has 0–3 double bounds; wherein the nitrogen and sulfur atom maybe optionally oxidized; wherein the nitrogen and sulfur heteroatoms may be optionally quartemized; and including any bicyclic group in which any of the above heterocyclic rings is fused to a benzene ring or another 5- or 6-membered heterocyclic ring independently defined above. Heterocyclics in which nitrogen is the heteroatom are preferred. Fully saturated heterocyclics are also preferred. Preferred heterocycles include: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substituents independently selected from hydroxy, halo, oxo (C=O), alkylimino (RN= wherein R is a loweralkyl group), amino, alkylamino, dialkylamino, acylaminoalkyl, alkoxy, thioalkoxy, polyalkoxy, loweralkyl, cycloalkyl or haloalkyl. The most preferred heterocyclics include imidazolyl, pyridyl, piperazinyl, azetidinyl, thiazolyl, triazolyl and the following:

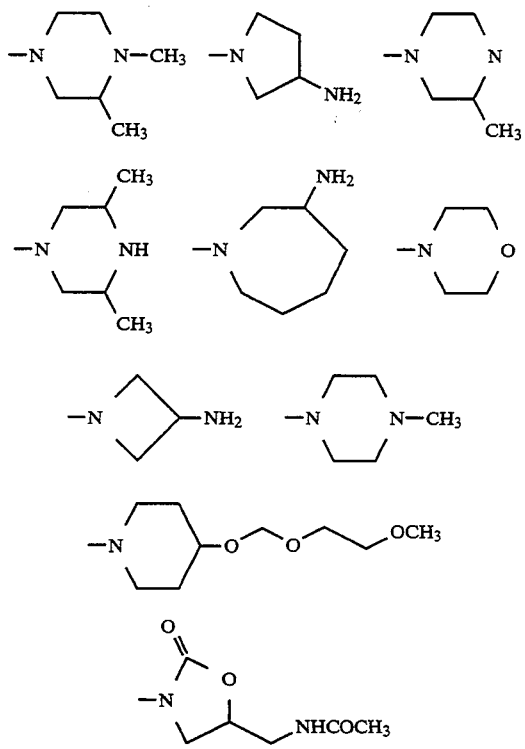

Representative compounds of the invention include, for example, 6H-benzofuro[3,2-c][1]benzopyran, 3,9-dihydroxy-2,10-di(N,N-(4-methyl-piperazinyl) methylene carboxamide)-6a,11a-cis-dihydro-6H-benzofuro[3,2-c][1]benzopyran, 3,9-dihydroxy-2,10-di(N-(3-methyl-2-butenyl) methylene carboxamide)-6a, 11a-cis-dihydro-6H-benzofuro[3,2-c][1]benzopyran, 3,9-di-hydroxy-2,10-di(N-octyl methylenecarboxamide)-6a, 11a-cis-dihydro-6H-benzofuro[3,2-c][1]benzopyran, 3,9-dihydroxy-2,10-di(N,N-dibenzyl methylenecarboxamide)-6a,11a-cis-dihydro-6H-benzofuro[3,2-c][1]benzopyran, 3,9-dihydroxy-2,10-di(N-morpholinyl methylenecarboxamide)-6a,11a-cis-dihydro-6H-benzofuro[3,2-c][1]benzopyran, 3,9-dihydroxy-2,10-di(dimethylaminoethylene)-6a,11a-cis-dihydro-6H-enzofuro[3,2-c][1]benzopyran, 3,9-dihydroxy-2,10-di(dibenzylaminoethylene)-6a,11a-cis-dihydro-6H-benzofuro-3,2-c][1]benzo-pyran, 3,9-dihydroxy-2,10-di(4-methylpiperazinylethylene)-6a,11a-cis-dihydro-6H-benzofuro[3,2-c][1]benzopyran. 3,9-dihydroxy-2,10-di(morpholinylethylene)-6a,11a-cis-dihydro-6H-benzofuro[3,2-c][1]benzopyran, 3,9-dihydroxy-2,10-diamino-methylene-6a,11a-cis-dihydro-6H-benzofuro[3,2-c][1 ]benzopyran N,N-dimethyl urea, 3,9-dihydroxy-2,10-diaminomethylene-6a,11a-cis-dihydro-6H-benzofuro[ 3,2-c][1]benzopyran N,N-dibenzyl urea, 3,9-dihydroxy-2,10-diamino-methylene-6a,11a-cis-dihydro-6H-benzofuro[3,2-c][1]benzopyran N,N-(4-methyl-piperazine) urea, and 3,9-dihydroxy- 2,10-diaminomethylene-6a,11a-cis-dihydro-6H-benzofuro[3,2-c][1]benzopyran 3-pyridinylmethylcarbamate.

The compounds of the present invention may be synthesized in accordance with the reaction scheme set forth in FIG. 1. As shown in FIG. 1, the scheme illustrates the preparation of 2,10 disubstituted isoflavonoid compounds in which methylenecarboxamides, aminoethylene, and aminomethylene ureas and carbamates are substituted at C(2) and C(10). In addition, 4-substituted isoflavonoid derivatives can be prepared by the metalation of compound 2a and trapping the resultant anion with an electrophile. Cyclization of erythrabyssin II to 2a is effected using acid catalyst (for example, p-toluenesulfonic acid, HCl, methanesulfonic acid, trifluoroacetic acid, Lewis acids ($BF_3$, $TiCl_4$ and the like) or sulfuric acid) in a solvent, such as toluene, tetrahydrofuran (THF), dioxane or dichloromethane, at ambient temperature to reflux temperature. Erythrabyssin II can also be cyclized by heating the compound at high temperature 200°–300° C. in a melt or high boiling solvent. The metalation of compound 2a is accomplished with alkyllithium reagents (for example, t-butyllithium, n-butyllithium and sec-butyllithium) in dry solvents (THF, ether, dioxane) with tetramethylethylenediamine (TMEDA) as an additive. The resultant anion is trapped with electrophiles to give 4-substituted compounds. The bis-pyran ring can be cleaved using trimethylsilyl iodide in solvents such as acetonitrile, chloroform, or dichloroethane at reflux temperature to give the dihydroxy compound 1b. The hydroxy groups are protected with groups such as trialkylsilyl, acetyl, benzyl, tetrahydropyranyl, methoxymethyl, benzyloxymethyl, methyl, methylthiomethyl and the like). The olefin is oxidatively cleaved using ruthenium tetraoxide, potassium permanganate, ozone/Jones reagent, ozone/NaOCl and the like to give the carboxylic acid. Reaction the carboxylic acid with a activating reagent selected from but not limited to carbonyldiimidazole (CDI), dicyclohexylcarbodiimide (DCC)/hydroxybenzotriazole (HOBT), 2-[1H-benzotriazole-1-yl]-1,1,3,3-tetramethyluronium hexaflurophosphate (HBTU), thionyl chloride, oxalyl chloride and the like and addition of an amine or alcohol give an amide or ester, respectively. In addition, reaction of the dicarboxylic acid 3 with triethylamine and diphenylphosphoryl azide in toluene at 70°–100° C. produces an isocyanate which maybe reacted with an amine or an alcohol to give a urea or carbamate, respectively. The amides are reduced to aminoethylene compounds 6 using hydride reducing reagents such as lithium aluminum hydride in THF.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearoyl chlorides, bromides and iodides, aralkyl halides like benzyl and phenethyl bromides, and others. Water or oil-soluble or dispersible products are thereby obtained.

Examples of acids which may be employed to form pharmaceutical acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful (in humans) for treating mycobacterial and other Gram-positive infections.

Total daily dose administered to a host in single or divided doses bay be in amounts, for example, from 0.001 to 1000 mg/kg body weight daily and more preferred from 1.0 to 30 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in $\frac{1}{3}$- propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., "Methods in Cell Biology," Volume XIV, Academic Press, New York, N.W. (1976), p. 33 et seq.

While the compounds of the invention can be administered as the sole active pharmaceutical agent, they can also be used in combination with one or more other antiinfective agents known to those skilled in the art. Representative examples of antiinfective agents that may be used in combination with the compounds of the invention include, without limitation, aminoglycosides such as streptomycin, neomycin, kanamycin, gentamicin, tobramycin, amikacin and netilmicin; erythromycin; lincomycin; clindamycin; tetracyclines such as oxytetracycline, tetracycline, demeclocycline, methacycline, doxycycline, and minocycline; chloramphenicol; vancomycin; metronidazole; rifampin; isoniazid; ethambutol; spectinomycin; polypeptides such as bacitracin; sulfonamides such as sulfisoxazole, sulfamethoxazole and sulfadiazine; trimethoprim; nitrofurantoin; nalidixic acid; cinoxacin; methenamine mandelate; methenamine hippurate; antiviral drugs such as amantadine, ribavirin, idoxuridine, vidarabine; and the like.

The above compounds to be employed in combination with the isoflavonoid compounds of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other antiinfective agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

When administered as a combination, the therapeutic agents can be formulated as separate compositions which are given at the same time or different times, or the therapeutic agents can be given as a single composition.

The foregoing may be better understood by reference to the following examples which are provided for illustration and not intended to limit the scope of the inventive concept. In the examples, compound reference numbers correspond to the compounds illustrated in the synthesis scheme of FIG. 1.

EXAMPLE 1

Bicyclicpterocarpan 2a from
3,9-Dihydroxy-2,10-(3-methyl-2-butenyl)-6a,11a-cis-dihydro-6H-benzofuro[3,2-c][1]benzopyran
(erythrabyssin II)

A solution of 10 mmol of erythrabyssin II, obtained from the root bark of *Erythrina variegata* according to the procedures of L. Mitscher et al., Phytochemistry, 29:2005, 1990, and 500 mg of p-toluenesulfonic acid monohydrate in 200 mL of toluene is heated at reflux temperature for 18 h, cooled and washed with saturated bicarbonate. The organic solution is concentrated to give an oil. Silica gel chromatography (hexane:ethyl acetate) gives the product.

EXAMPLE 2

4-Bromobicyclicpterocarpan 2b. General Procedure for the Metalation of 2a

A solution of t-butyllithium (5.5 mmol) in pentane is added to tetramethylethylenediamine (5.5 mmol) in 50 mL of dry tetrahydrofuran at −70° C. A solution of 2a (5.0 mmol) is added dropwise over a 30 min period. The resulting solution is stirred for 60 min. Bromine (5.5 mmol) is added such that the temperature does not exceed 60° C. After stirring for 30 min the bath is removed and the reaction is quenched with 2N HCl (final pH 6.0). The reaction mixture is warmed to room temperature and extracted with ether. The ether extracts are washed with water, dried (MgSO$_4$) and concentrated. Silica gel chromatography (hexane:ethyl acetate) gives the product.

EXAMPLE 3

General Procedure for the Cleavage of the Pyran Ring. Preparation of 4-Bromo-3,9-Dihydroxy-2,10-(3-methyl-2-butenyl)-6a,11a-cis-dihydro-6H-benzofuro[3,2-c][1]benzopyran 1b A solution of bromide 2b (2.0 mmol) and excess trimethylsilyl iodide are heated in acetonitrile at reflux temperature for 18 h. The reaction is cooled, 2N HCl is added and the mixture is stirred an additional 3 h. Chloroform is added and the layers are separated. The aqueous layer is extracted with chloroform and the combined chloroform extracts are dried and concentrated. The title compound is obtained pure by flash silica gel chromatography using ethyl acetate:hexane as eluent.

EXAMPLE 4

3,9-Dihydroxy-2,10-(3-methyl-2-butenyl)-6a,11a-cis-dihydro-6H-benzofuro[3,2-c][1]benzopyran Di-t-butyldimethylsilyl Ether A solution of 2.5 mmol of erythrabyssin II (1a), t-butyldimethylsilyl chloride 6.0 mmol, and imidazole 6.0 mmol are stirred in 25 mL of DMF at room temperature for 18 h. Chloroform (100 mL) is added and the organic solution is washed with saturated sodium bicarbonate, dried (MgSO4) and concentrated. Silica gel chromatography of the residue gives the title compound.

EXAMPLE 5

3,9-Dihydroxy-2,10-di(methylenecarboxylic acid-6a,11a-cis-dihydro-6H-benzofuro[3,2-c][1]benzopyran Di-t-butyl dimethylsilyl Ether (3)

Using the procedure of Carlsen et al., *J. Org. Chem.* 46:3936–3938, 1981, a solution of olefin 1a (2.0 mmol), NaIO4 (21 mmol) in 8 mL of carbon tetrachloride, 8 mL acetonitrile and 12 mL of water is stirred while a catalytic amount of RuCl3 H2O (0.1 mmol) is added. The mixture is stirred for 6 h at ambient temperature, filtered through a pad of celite and concentrated. Evaporation of the solvents gives the diacid 3.

EXAMPLE 6

3,9-Dihydroxy-2,10-di(N,N-dimethyl methylenecarboxamide)-6a,11a-cis-dihydro-6H-benzofuro[3,2-c][1]benzopyran Di-t-butyl dimethylsilyl Ether (4)

A solution of diacid 3 (1.0 mmol) in THF and carbonyl diimidazole (2.0 mmol) are stirred at room temperature for 30 min and dimethylamine (excess) is bubbled through the reaction for 15 min. The reaction is stirred an additional 2 h and the solvents are evaporated. The diamide is obtained pure by silica gel chromatography using ethyl acetate:hexane as eluent.

EXAMPLE 7

3,9-Dihydroxy-2,10-di(N,N-dimethyl methylenecarboxamide)-6a,11a-cis-dihydro-6H-benzofuro[3,2-c][1]benzopyran (5)

The disilyl ether 4 (prepared in Example 6, 0.5 mmol) is dissolved in chloroform and excess tetrabutylammonium fluoride in THF is added. The reaction is stirred for 3 h, water is added and the chloroform layer is separated, dried, and concentrated. The title compound is obtained pure by silica gel chromatography.

EXAMPLE 8

3,9-Dihydroxy-2,10-di(N,N-(4-methylpiperazinyl) methylene carboxamide)-6a,11a-cis-dihydro-6H-benzofuro[3,2-c][1]benzopyran Using the procedures in Examples 6 and 7 and replacing dimethylamine with N-methylpiperazine gives the title compound.

EXAMPLE 9

3,9-Dihydroxy-2,10-di(N-(3-methyl-2-butenyl) methylene carboxamide)-6a,11a-cis-dihydro-6H-benzofuro[3,2-c][1]benzopyran Using the procedures in Examples 6 and 7 and replacing dimethylamine with 1-amino-3-methyl-2-butene gives the title compound.

EXAMPLE 10

3,9-Dihydroxy-2,10-di(N-octylmethylenecarboxamide)-6a,11a-cis-dihydro-6H-benzofuro[3,2-c][1]benzopyran Using the procedures in Examples 6 and 7 and replacing dimethylamine with octylamine gives the title compound.

EXAMPLE 11

3,9-Dihydroxy-2,10-di(N,N-dibenzyl methylenecarboxamide)-6a,11a-cis-dihydro-6H-benzofuro[3,2-c][1]benzopyran Using the procedures in Examples 6 and 7 and replacing dimethylamine with dibenzylamine gives the title compound.

EXAMPLE 12

3,9-Dihydroxy-2,10-di(N-morpholinyl methylenecarboxamide)-6a,11a-cis-dihydro-6H-benzofuro[3,2-c][1]benzopyran Using the procedures in Examples 6 and 7 and replacing dimethylamine with morpholine gives the title compound.

EXAMPLE 13

3,9-Dihydroxy-2,10-di(dimethylaminoethylene),6a,11a-cis-dihydro-6H-enzofuro[3,2-c][1]benzopyran (6)

The compound prepared in Example 6 (1 mmol) is added to a suspension of lithium aluminum hydride (6 mmol) in 25 mL of THF at 0°–5° C. The reaction is stirred for 18 h to room temperature, recooled in an ice-water bath and quenched with 6N HCl. The reaction is stirred an additional 18 h and neutralized with saturated sodium bicarbonate to pH 8. The product is extracted into CHCl3 and chloroform extracts are dried and concentrated. Chromatography of the oily residue (CHCl3:methanol:NH4OH) gives the product.

EXAMPLE 14

3,9-Dihydroxy-2,10-di(dibenzylaminoethylene)-6a,11a-cis-dihydro-6H-benzofuro[3,2-c][1]benzopyran Using the procedure in Example 13 and substituting the compound prepared in Example 6 with the compound prepared in Example 11 gives the product.

EXAMPLE 15

3,9-Dihydroxy-2,10-di(4-methylpiperazinylethylene)-6a,11a-cis-dihydro-6H-benzofuro[3,2-c][1]benzopyran Using the procedure in Example 13 and substituting the compound prepared in Example 6 with the compound prepared in Example 8 gives the product.

EXAMPLE 16

3,9-Dihydroxy-2,10,-di(morpholinylethylene)-6a,11a-cis-dihydro-6H-benzofuro[3,2-c][1]benzopyran Using the procedure in Example 13 and substituting the compound prepared in Example 6 with the compound prepared in Example 12 gives the product.

EXAMPLE 17

3,9-Dihydroxy-2,10-diaminomethylene-6a,11a-cis-dihydro-6H-benzofuro[3,2-c][1]benzopyran N,N-Dimethyl Urea Dicarboxylic acid 3 (prepared in Example 5, 2 mmol), triethylamine (4 mmol), diphenylphosphoryl azide (4.2 mmol) in 20 mL of dry toluene are heated at 70° C. for 2 h. The reaction is cooled to room temperature and dimethylamine is bubbled through the toluene solution for 30 min. The reaction mixture is stirred for an additional 6 h. The solvents are evaporated and the residue is dissolved in 10 mL of CHCl$_3$ and treated with tetrabutylammonium fluoride (15 mmol). After 6 h the solvents are concentrated and 6N HCl (2 mL) is added along with 10 mL of THF. The aqueous THF solution is stirred for 18 h and extracted with CHCl$_3$. The chloroform extracts are dried (MgSO$_4$) and concentrated. The residue is purified by silica gel chromatography to give the title compound.

EXAMPLE 18

3,9-Dihydroxy-2,10-diaminomethylene-6a,11a-cis-dihydro-6H-benzofuro[3,2-c][1]benzopyran N,N-Dibenzyl Urea Using the procedure in Example 17 and substituting dibenzylamine for dimethylamine gives the product.

EXAMPLE 19

3,9-Dihydroxy-2,10-diaminomethylene-6a,11a-cis-dihydro-6H-benzofuro[3,2-c][1]benzopyran N,N-(4-Methylpiperazine) Urea Using the procedure in Example 17 and substituting 4-methylpiperazine for dimethylamine gives the product.

EXAMPLE 20

3,9-Dihydroxy-2,10-diaminomethylene-6a,11a-cis-dihydro-6H-benzofuro[3,2-c][1]benzopyran 3-pyridinylmethylcarbamate Using the procedure in Example 17 and substituting 3-pyridinylcarbinol for dimethylamine and heating the reaction mixture for 2 h gives the product. The antibacterial activity is determined by the procedures of L. Mitscher et al. *J. Natural Products* 50:1025-1040, 1987, *Phytochemistry* 27:3449-52, 1988, and *Phytochemistry* 27:381-385, 1988; M. O'Neill et al. Phytochemistry, 25:1315-22, 1986; K. Nakanishi et al. *Heterocycles*, 15:1163-70, 1981; and M. Iinuma, *Chem. Pharm. Bull.*, 40:2749-52, 1992.

While the presently preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound of formula (I) or (II):

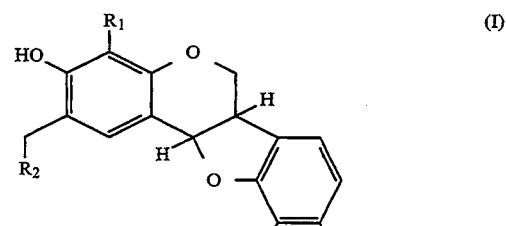

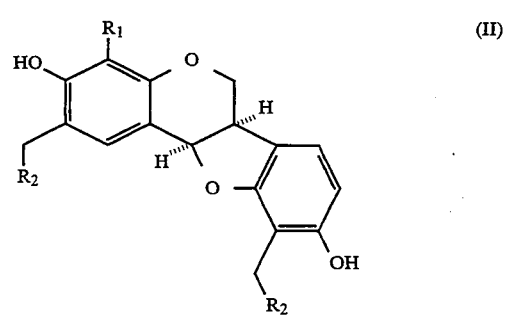

wherein R$_1$ is hydrogen or bromine; and

R$_2$ is selected from the group consisting of —CONR$_4$R$_5$, —(CH$_2$)$_n$—NR$_4$R$_5$, —NHCO—NR$_4$R$_5$ and —NHCO$_2$R$_4$, wherein R$_4$ and R$_5$ are selected from hydrogen, loweralkyl, alkoxy, cycloalkyl, cycloalkylalkyl, aryl, arylalkyl, arylalkylaryl, arylaryl, aryoxy, aryloxyaryl, aryloxyarylalkyl, arylalkoxy, arylalkoxyaryl, arylalkoxyarylalkyl, arylalkoxyaryl, alkenyl, alkynyl and heterocycle, or R$_4$ and R$_5$ are connected to form a ring and produce cycloalkyl or heterocycle; and n is 1; or a pharmaceutically acceptable salt thereof.

2. A compound as defined by claim 1 wherein R$_2$ is —CONR$_4$R$_5$ wherein R$_4$ and R$_5$ are selected from hydrogen, loweralkyl, cycloalkyl, cycloalkylalkyl, aryl, arylalkyl, aryloxyaryl, aryloxyarylalkyl, arylalkoxyarylalkyl, arylalkoxyaryl, alkenyl and alkynyl, or R$_4$ and R$_5$ are taken together to form cycloalkyl or heterocycle; and R$_1$ is hydrogen or halogen; or a pharmaceutically acceptable salt thereof.

3. A compound of claim 2 wherein R$_4$ and R$_5$ are loweralkyl, aryloxyarylalkyl, alkenyl or alkynyl, or R$_4$ and R$_5$ are taken together to form cycloalkyl, or a pharmaceutically acceptable salt thereof.

4. A compound as defined by claim 3 wherein R$_4$ and R$_5$ are methyl or 3-methyl-2-butenyl, and R$_1$ is hydrogen; or a pharmaceutically acceptable salt thereof.

5. A method of inhibiting the growth of gram-positive organisms comprising contacting the gram-positive organisms with a growth inhibitory amount of a compound of formula (I) or (II):

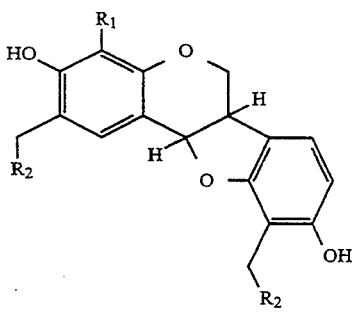

(I)

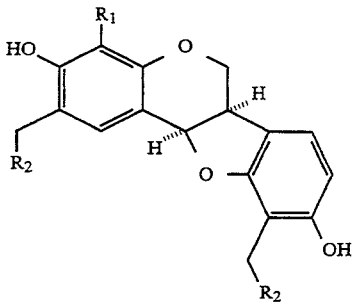

(II)

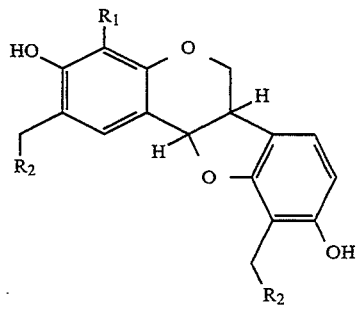

(I)

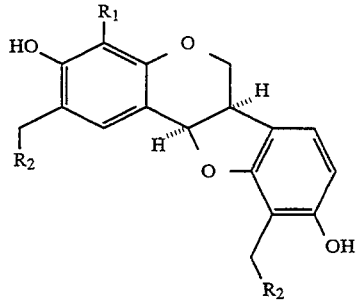

(II)

wherein $R_1$ is hydrogen or bromine; and $R_2$ is selected from the group consisting of —$CONR_4R_5$, —$(CH_2)_n$—$NR_4R_5$, —NHCO—$NR_4R_5$ and —$NHCO_2R_4$, wherein $R_4$ and $R_5$ are selected from hydrogen, loweralkyl, alkoxy, cycloalkyl, cycloalkylalkyl, aryl, arylalkyl, arylalkylaryl, arylaryl, aryoxy, aryloxyaryl, aryloxyarylalkyl, arylalkoxy, arylalkoxyaryl, arylalkoxyarylalkyl, arylalkoxyaryl, alkenyl, alkynyl and heterocycle, or $R_4$ and $R_5$ are connected to form a ring and produce cycloalkyl or heterocycle; and n is 1; or a pharmaceutically acceptable salt thereof.

6. A method of claim 5 wherein $R_2$ is —$CONR_4R_5$ wherein $R_4$ and $R_5$ are selected from hydrogen, loweralkyl, cycloalkyl, cycloalkylalkyl, aryl, arylalkyl, aryloxyaryl, aryloxyarylalkyl, arylalkoxyarylalkyl, arylalkoxyaryl, alkenyl and alkynyl, or $R_4$ and $R_5$ are taken together to form cycloalkyl or heterocycle; and $R_1$ is hydrogen or halogen, or a pharmaceutically acceptable salt thereof.

7. A method of claim 6 wherein $R_4$ and $R_5$ are loweralkyl, aryloxyarylalkyl, alkenyl or alkynyl, or $R_4$ and $R_5$ are taken together to form cycloalkyl, or a pharmaceutically acceptable salt thereof.

8. A method of claim 7 wherein $R_4$ and $R_5$ are methyl or 3-methyl-2-butenyl, and $R_1$ is hydrogen; or a pharmaceutically acceptable salt thereof.

9. The method of claim 6 wherein the gram-positive organism is selected from the group consisting of *Mycobacteria tuberculosis*, *Mycobacteria leprae*, and *Mycobacteria avium* complex.

10. The method of claim 9 wherein the gram-positive organism is *Mycobacteria tuberculosis*.

11. The method of claim 10 wherein the gram-positive organism is a multidrug-resistant strain of *Mycobacteria tuberculosis*.

12. A method of treating a human or animal subject suffering from a pathogenic infection by a gram-positive organism in need of such treatment comprising administering to the subject a therapeutically effective amount of a compound of formula (I) or (II):

wherein $R_1$ is hydrogen or bromine; and $R_2$ is selected from the group consisting of —$CONR_4R_5$, —$(CH_2)_n$—$NR_4R_5$, —NHCO—$NR_4R_5$ and —$NHCO_2R_4$, wherein $R_4$ and $R_5$ are selected from hydrogen, loweralkyl, alkoxy, cycloalkyl, cycloalkylalkyl, aryl, arylalkyl, arylalkylaryl, arylaryl, aryoxy, aryloxyaryl, aryloxyarylalkyl, arylalkoxy, arylalkoxyaryl, arylalkoxyarylalkyl, arylalkoxyaryl, alkenyl, alkynyl and heterocycle, or $R_4$ and $R_5$ are connected to form a ring and produce cycloalkyl or heterocycle; and n is 1; or a pharmaceutically acceptable salt thereof.

13. A method of claim 12 wherein $R_2$ is —$CONR_4R_5$ wherein $R_4$ and $R_5$ are selected from hydrogen, loweralkyl, cycloalkyl, cycloalkylalkyl, aryl, arylalkyl, aryloxyaryl, aryloxyarylalkyl, arylalkoxyarylalkyl, arylalkoxyaryl, alkenyl and alkynyl, or $R_4$ and $R_5$ are taken together to form cycloalkyl or heterocycle; and $R_1$ is hydrogen or halogen, or a pharmaceutically acceptable salt thereof.

14. A method of claim 13 wherein $R_4$ and $R_5$ are loweralkyl, aryloxyarylalkyl, alkenyl or alkynyl, or $R_4$ and $R_5$ are taken together to form cycloalkyl, or a pharmaceutically acceptable salt thereof.

15. A method of claim 14 wherein $R_4$ and $R_5$ are methyl or 3-methyl-2-butenyl, and $R_1$ is hydrogen; or a pharmaceutically acceptable salt thereof.

16. The method of claim 12 wherein the human or animal subject is suffering from a pathogenic infection by a mycobacteria selected from the group consisting of *Mycobacteria tuberculosis*, *Mycobacteria leprae*, and *Mycobacteria avium* complex.

17. A pharmaceutical composition comprising an antibacterially effective amount of a compound according to claim 1 together with a pharmaceutically acceptable carrier.

18. A pharmaceutical composition comprising an antibacterially effective amount of a compound according to claim 2 together with a pharmaceutically acceptable carrier.

19. A method of treating staphlococal infections comprising administering to a mammal in need of such treatment a therapeutically effective amount of a compound as defined by claim 1.

* * * * *